United States Patent [19]

Wardle et al.

[11] Patent Number: 5,739,325
[45] Date of Patent: Apr. 14, 1998

[54] HYDROGENOLYSIS OF 2,4,6,8,10,12-HEXABENZYL-2,4,6,8,10,12-HEXAAZATETRACYCLO[5.5.0.0$^{5,9}$.0$^{3,11}$] DODECANE

[75] Inventors: Robert B. Wardle, Logan; W. Wayne Edwards, Tremonton, both of Utah

[73] Assignee: Thiokol Corporation, Ogden, Utah

[21] Appl. No.: 568,451

[22] Filed: Dec. 7, 1995

[51] Int. Cl.$^6$ .................................................. C07D 255/04
[52] U.S. Cl. ........................................ 540/554; 149/92
[58] Field of Search ........................... 149/92; 540/554, 540/556; 546/1; 564/107, 141, 144

[56] References Cited

U.S. PATENT DOCUMENTS

| | | | |
|---|---|---|---|
| 2,459,002 | 1/1949 | Parker et al. | 564/144 X |
| 2,485,855 | 10/1949 | Blomquist et al. | 149/92 X |
| 3,228,929 | 1/1966 | Frankel | 540/554 |
| 3,535,390 | 10/1970 | Driscoll | 149/88 X |
| 4,432,902 | 2/1984 | McGuire et al. | 149/92 X |
| 4,485,237 | 11/1984 | Willer | 149/92 X |
| 4,487,938 | 12/1984 | Boileau et al. | 548/304 |
| 5,124,493 | 6/1992 | Lukasavage et al. | 149/92 X |
| 5,409,617 | 4/1995 | Ross et al. | 210/762 |

OTHER PUBLICATIONS

Anthony J. Bellamy, "Reductive Debenzylation of Hexabenzyl–hexaazaisowurtizitane," *Tetrahedron*, vol. 51, No. 16, pp. 4711–4722 (1995).

Chemical Abstracts, 120: 221757a, Propellants and Explosives, "Synthesis and explosive performance characteristics of polynitro polycyclic cage explosives", vol. 120, p. 232 (1994).

Chemical Abstracts, 121: 38726w, Propellants and Explosives, "The thermal stability of the polymorphs of hexanitrohexaazaisowurt zitane", vol. 121, p. 186 (1994).

Chemical Abstracts, 120: 32623e, Propellants and Explosives, "Thermal stability of hexanitrohexaazaisowurtzitane in an Estane formulation", vol. 120, (1994).

Chemical Abstracts, 120: 248721w, Propellants and Explosives, "The thermal stability of the polymorphs of hexanitrohexaazaisowurt zitane. Part I", vol. 120, (1994).

Chemical Abstracts, 120: 221778h, Propellants and Explosives, "Diagnostic scheme for polynitrocage compounds", vol. 120 (1994).

Arnold T. Nielsen et al., Polyazapolycyclics by Condensation of Aldehydes with Amines. 2. Formation of 2,4,6,8,10,12-Hexabenzyl-2,4,8,10,12-hexaazatetracyclo [5.5.0.0$^{5,9}$.0$^{3,11}$] dodecanes from Glyoxal and Benzylamines[1,2], *Journal of Organic Chemistry*, vol. 55, pp. 1459–1466(1990).

*Primary Examiner*—Richard D. Lovering
*Attorney, Agent, or Firm*—Cushman Darby & Cushman IP Group of Pillsbury Madison & Sutro, LLP; Ronald L. Lyons, Esq.

[57] ABSTRACT

A process for the hydrogenolysis of 2,4,6,8,10,12-hexabenzyl-2,4,6,8,10,12-hexaazatetracyclo[5.5.0.0$^{5,9}$.0$^{3,11}$] dodecane ("HBIW") is disclosed. In the process, a quantity of HBIW, a cosolvent, and a bromine source are placed into a reaction vessel. Acetic anhydride and a palladium hydrogenolysis catalyst are rapidly added to the reaction vessel. The hydrogenolysis catalyst should be substantially free of water. The reaction vessel is purged of an atmosphere capable of reacting with hydrogen, and hydrogen is quickly introduced into the reaction vessel to convert the HBIW to tetraacetyldibenzylhexaazaisowurtzitane ("TADB"). The acetic anhydride is added immediately prior to hydrogen introduction so that the acetic anhydride does not have time to react with the HBIW to form an acetylated derivative prior to commencement of the desired hydrogenation reaction. The process requires very little palladium catalyst, preferably less than 10% wt/wt based on the HBIW substrate. The TADB, precipitated on the palladium hydrogenolysis catalyst, is subjected to a second hydrogenation step using a formic acid solvent in the presence of hydrogen to form tetraacetyldiformylhexaazaisowurtzitane ("TADF").

27 Claims, No Drawings

HYDROGENOLYSIS OF 2,4,6,8,10,12-HEXABENZYL-2,4,6,8,10,12-HEXAAZATETRACYCLO[5.5.0.0$^{5,9}$.0$^{3,11}$] DODECANE

GOVERNMENT RIGHTS

The U.S. Government has a certain rights in this invention as provided for by the terms of contract No. N00014-91-C-0254 awarded by the Office of Naval Research.

FIELD OF THE INVENTION

The present invention relates to the hydrogenolysis of 2,4,6,8,10,12-hexabenzyl-2,4,6,8,10,12-hexaazatetracyclo-[5.5.0.0$^{5,9}$.0$^{3,11}$]dodecane, sometimes referred to as "hexabenzylhexaazaisowurtzitane" and hereinafter referred to as "HBIW."

BACKGROUND OF INVENTION

An important step in the synthesis of 2,4,6,8,10,12-hexanitro-2,4,6,8,10,12-hexaazatetracyclo[5.5.0.0$^{5,9}$.0$^{3,11}$] dodecane, sometimes referred to as "HNIW" or "CL-20," is the hydrogenolysis of the chemical intermediate HBIW. HBIW can be synthesized according to the procedure described by Nielsen et al., "Polyazapolycyclics by Condensation of Aldehydes with Amines. 2. Formation of 2,4,6,8,10,12-Hexabenzyl-2,4,6,8,10,12-hexaazatetracyclo [5.5.0.0$^{5,9}$.0$^{3,11}$]dodecanes from Glyoxal and Benzylamines," *Journal of Organic Chemistry*, Vol. 55, pp. 1459–66, (1990). An improvement to the hydrogenolysis of HBIW would represent an improvement in the overall synthesis of CL-20.

CL-20 is a polycyclic caged nitramine oxidizer. For most existing weapons systems, the most critical ingredient in both propellant and explosive applications is the oxidizer. CL-20, with its substantial increase in performance output, represents a major breakthrough in energy capabilities for future propellant and explosive systems. It may be possible to replace existing weapons system energetic fills with CL-20 to increase shaped charge anti-armor penetration, increase missile payload velocity and standoff, increase underwater torpedo effectiveness and lethality, and improve gun propellant impetus.

The current open literature techniques of HBIW hydrogenolysis are reported by Anthony J. Bellamy, "Reductive DebenzylationofHexabenzylhexaazaisowurtzitane," *Tetrahedron*, Vol. 51, No. 16, pp. 4711–22 (1995). A representation of the current hydrogenolysis step is set forth below:

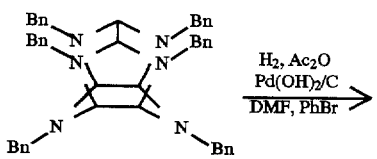

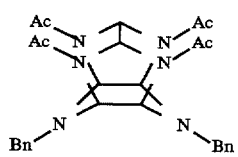

The product is tetraacetyldibenzylhexaazaisowurtzitane ("TADB"). Bellamy reports the catalytic hydrogenation of HBIW under a variety of conditions with the objective to find conditions which would effect partial or complete debenzylation of HBIW. The yield of toluene was used as an indicator of the extent of reductive debenzylation. When the toluene yield was low, the recovery of starting material was usually high, whereas in those experiments where reasonable yields of the tetrabenzylated product were obtained, the toluene yield was at or slightly below 4 mmol per mmol of starting material.

Bellamy's experiments used 1 mmol HBIW (708 mg) in combination with various solvents, acetylating agents, and hydrogenation catalysts. The following different hydrogenation catalysts were tested by Bellamy: dried Degussa type E101 NE/W 10% Pd on activated carbon, dried Pearlman's catalyst (palladium hydroxide on carbon, 20% Pd), and moist Pearlman's catalyst. The catalysts were used at quantities from 70 mg to 710 mg (10% wt/wt to 100% wt/wt based on HBIW substrate). According to Bellamy, at least 50% wt/wt and preferably 100% wt/wt catalyst, based on HBIW substrate, was necessary to achieve acceptable debenzylation of the HBIW.

The palladium-based catalyst used in the hydrogenolysis step represent a major expense in the overall cost to synthesize CL-20. Arnold T. Nielsen has reported that the catalyst cost is over $200 per pound of CL-20 ultimately produced. See, copending application Ser. No. 07/292,028, filed Dec. 21, 1988 and Ser. No. 07/989,369, filed Dec. 8, 1992, and the references cited therein, which applications and references are incorporated herein by reference.

In the original synthesis of CL-20 reported by Arnold T. Nielsen, "Synthesis of Polynitropolyaza Caged Nitramines," *Chemical Propulsion Information Agency (CPIA)*, publication number 473, December 1987, the TADB is converted to CL-20 via a dinitroso intermediate, teraacetyldinitrosohexaazaisowurtzitane, as shown below:

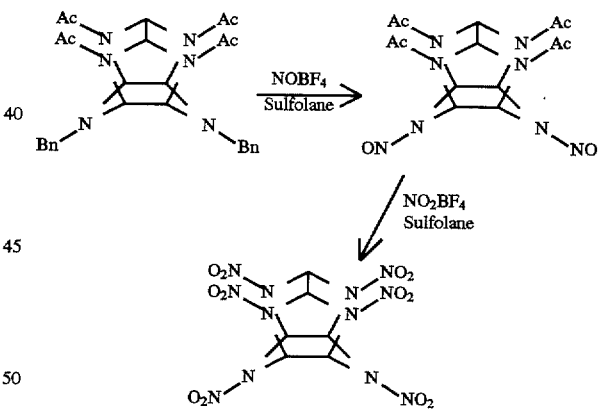

Although effective, this route uses large amounts of Pd(OH)$_2$/carbon and the expensive BF$_4$-based nitrating agents.

An improvement to the Nielsen route for the cleavage of the final benzyl groups is depicted below:

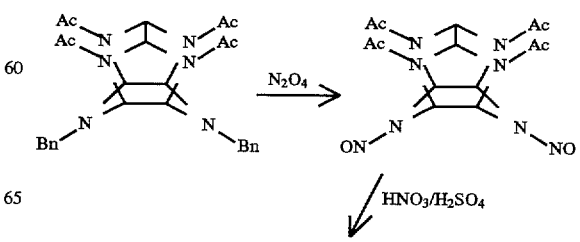

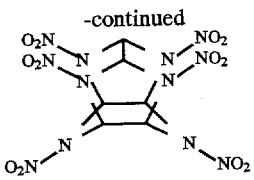

-continued

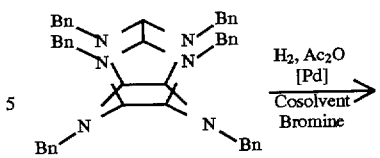

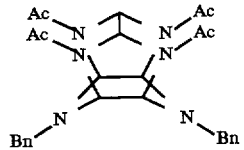

As explained in greater detail in copending application Ser. Nos. 07/292,028 and 07/989,369, it would be an advancement in the art to avoid the formation of the dinitroso intermediate and the need for expensive $BF_4$-based reagents and to provide a simpler route for the formation of CL-20.

It would be a further significant advancement in the art to provide a process for the hydrogenolysis of 2,4,6,8,10,12-hexabenzyl-2,4,6,8,10,12-hexaazatetracyclo[5.5.0.0$^{5,9}$.0$^{3,11}$]dodecane which requires less catalyst than currently known processes, thereby reducing the overall manufacturing cost of CL-20. It would also be an advancement in the art to provide a process for the hydrogenolysis of 2,4,6,8,10,12-hexabenzyl-2,4,6,8,10,12-hexaazatetracyclo[5.5.0.0$^{5,9}$.0$^{3,11}$]dodecane which produces high yields of the desired end product.

SUMMARY OF THE INVENTION

The present invention is directed to a process for the hydrogenolysis of 2,4,6,8,10,12-hexabenzyl-2,4,6,8,10,12-hexaazatetracyclo[5.5.0.0$^{5,9}$.0$^{3,11}$]dodecane ("HBIW"). In the process, a quantity of HBIW, a cosolvent, and a bromine source are placed into a reaction vessel. Acetic anhydride and a palladium hydrogenolysis catalyst are added to the reaction vessel, followed immediately by introduction of hydrogen into the reaction vessel. Once hydrogen is introduced into the reaction vessel, the HBIW is converted to tetraacetyldibenzylhexaazaisowurtzitane ("TADB"). The acetic anhydride is added immediately prior to hydrogen introduction so that the acetic anhydride does not have time to react with the HBIW to form an acetylated derivative prior to commencement of the desired hydrogenation reaction.

The hydrogenolysis catalyst should be substantially free of water to inhibit unwanted reaction byproducts. This can be accomplished by washing with the cosolvent. The process requires very little palladium catalyst, preferably less than 10% wt/wt based on the HBIW substrate, and most preferably less than 5% wt/wt based on the HBIW substrate. The palladium hydrogenolysis catalyst preferably includes a carbon substrate wherein the palladium metal content relative to the carbon is less than 10% by weight, preferably less than 5%, and can even be used at concentrations less than 3%, by weight.

The TADB product precipitates on the palladium hydrogenolysis catalyst and is easily recovered by filtration. According to the disclosed process, the TADB is subjected to a second hydrogenolysis step using a formic acid solvent in the presence of hydrogen to form tetraacetyldiformylhexaazaisowurtzitane ("TADF").

DETAILED DESCRIPTION OF THE INVENTION

The present invention is directed to a process for the hydrogenolysis of 2,4,6,8,10,12-hexabenzyl-2,4,6,8,10,12-hexaazatetracyclo[5.5.0.0$^{5,9}$.0$^{3,11}$]dodecane ("HBIW"). The first step of the hydrogenolysis process is shown as follows:

According to the process, a quantity of HBIW and a cosolvent are introduced into a reaction vessel. Currently preferred cosolvents which have been shown to provide significant improvement are N,N-dimethylformamide ("DMF"), N-methylpyrollidone ("NMP"), and 1,2-dimethoxyethane. Of course, other known and novel cosolvents can be used, but they may not provide the same improvement in reproducibility and in reducing the catalyst loading as with the cosolvents mentioned above.

A bromine source is also added to the reaction vessel. Suitable bromine sources include molecules having active bromine, such as benzyl bromide, acetyl bromide, and bromine gas ($Br_2$). The order of bromine source addition is not critical to the present invention. The HBIW, cosolvent, and bromine source are preferably mixed in an atmosphere which is substantially non-reactive with hydrogen. For instance, the reaction vessel can be purged with an inert atmosphere, such as a nitrogen. Alternatively, the reaction vessel atmosphere can be removed by vacuum.

Acetic anhydride and a palladium hydrogenolysis catalyst are rapidly added to the reaction vessel. It is important that the acetic anhydride and palladium catalyst are added just before the reaction begins to inhibit formation of N-benzylacetamide which acts as a catalyst poison. N-benzylacetamide is formed by reaction of HBIW and acetic anhydride.

The hydrogenolysis catalyst is preferably added to the reaction vessel in an amount less than 10% wt/wt based on the HBIW substrate. Typical hydrogenolysis catalysts which can be used include Pd(OH)$_2$, Pd, and mixtures thereof on carbon commonly used as a catalyst support. Several standard palladium metal and Pearlman's-type catalysts have both been found to be suitable. Such catalysts are commercially available. Similarly, catalysts that are provided either water-wet or dry have been useful. The weight percent of active palladium on carbon is preferably less than 10%, more preferably less than 5%, and can be as low as 3%.

The hydrogenolysis catalyst is preferably substantially free of water. This can be accomplished by washing the catalyst with the cosolvent prior to introduction into the reaction vessel to remove water associated with the catalyst. The palladium catalyst is normally shipped water-wet, with approximately 50% of the weight being water. While not wishing to be bound by theory, it is presently believed that acetic acid, formed by reaction of acetic anhydride in the reaction mixture with the water on the catalyst, reduces the yield and increases the chances of a failed or incomplete reaction. Previous efforts at water removal, such as vacuum drying, which was unacceptable due to fire hazard and catalyst activity reduction, or washing with acetic anhydride, did not fully remove water and left acetic acid present. Washing with the polar cosolvent effectively removes water and does not introduce deleterious side products or reduce catalyst reactivity.

It has been discovered that addition of the reactive acetic anhydride immediately prior to hydrogen introduction improves the reaction yield, rate, and reproducibility. A major contributor to incomplete or low yield reactions is the formation of N-benzylacetamide which acts as a catalyst poison. N-benzylacetamide is formed by the acid catalyzed decomposition of HBIW to yield "free" benzyl amine followed by acetylation of the benzyl amine by acetic anhydride. This reaction occurs slowly once the reaction mixture is together. To minimize this unwanted reaction, the cosolvent and HBIW are preferably placed in the reaction vessel first, followed by the bromine source. The contents are thoroughly mixed and placed under a nitrogen atmosphere. The acetic anhydride and the washed palladium catalyst are then added quickly, followed immediately by hydrogen introduction. Once the acetic anhydride is added to the HBIW, the hydrogen must be added rapidly to inhibit unwanted side reactions.

Hydrogen introduction into the reaction vessel to begins conversion of HBIW to tetraacetyldibenzylhexaazaisowurtzitane ("TADB"). The TADB product is allowed to precipitate onto the catalyst and is not removed from the catalyst. The cosolvent assists in providing complete precipitation. After the hydrogenolysis is complete, the product and catalyst are filtered from the liquid phase and washed with a solvent, such as denatured ethanol, methanol, or isopropanol. The solvent is preferably miscible with the DMF, acetic anhydride, and acetic acid so that these compounds can be removed from the desired TADF product. The solvent is also preferably immiscible with the desired TADF product so that the TADF is not dissolved and washed away with the solvent. It is also important that the solvent have no effect on the subsequent hydrogenolysis reaction.

The filtered and washed TADB is sufficiently pure for a second hydrogenolysis reaction in which the TADB product and catalyst are reacted with formic acid to form tetraacetyldiformylhexaazaisowurtzitane ("TADF"). This route differs from the known CL-20 synthesis in using a second hydrogenolysis step, rather than $N_2O_4$, to remove the final two benzyl groups. The second hydrogenolysis reaction is shown below:

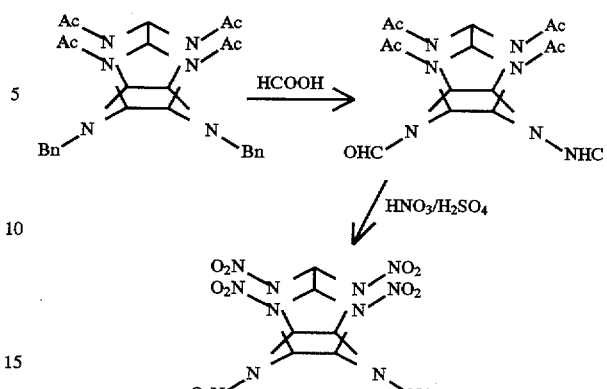

It has been found that the resident catalyst onto which the product from the first hydrogenolysis precipitated was sufficient for the second hydrogenolysis reaction, even at dramatically reduced catalyst loading for the first hydrogenolysis reaction.

The second hydrogenolysis is accomplished using formic acid as the solvent. While not wishing to be bound by theory, it is presently believed that formic acid plays an important role in the hydrogenolysis of TADB. It is postulated that the formic acid converts the benzylamine moiety into a benzylammonium formate functionality which is then hydrogenolyzed more readily, as shown below:

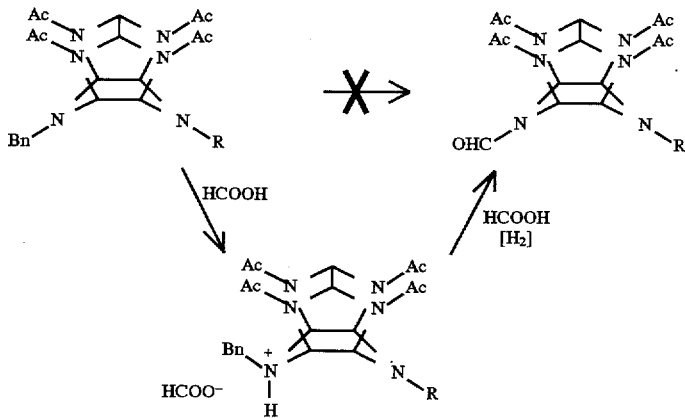

The hypothesis that protonation is the reason for success in the second hydrogenolysis reaction is supported by the fact that the used catalyst from the conversion of HBIW to TADB can also carry out the conversion of TADB to TADF with no modification of that catalyst or addition of a second catalyst. This establishes that the catalyst is not the limiting reagent in the removal of the final two benzyl groups. Rather, it suggests that a change in the substrate from containing a benzylamine moiety to a substrate containing a benzylammonium formate moiety causes this change in reactivity. Furthermore, experimental results show that when a more robust catalyst than 20% Pearlman's catalyst is used, such as Degussa E101 NE/W, 10% Pd), that catalyst is still effective in the first hydrogenolysis even after having been previously employed in both the first and second hydrogenolysis reactions. This complete recycle was demonstrated on a laboratory scale with a single 10% weight-to-weight catalyst loading, based on HBIW substrate.

The formic acid preferably has a concentration of 88%, which is the water azeotrope, so that recovery of the formic acid is simplified. In this way, the formic acid can be reused after a simple distillation. Of course, the concentration of formic acid can vary. However, if the formic acid concentration is too dilute, the desired diformyl product will not be obtained. The products which arise from the second hydrogenolysis reaction are dependant on the reaction medium. These products vary from the bis-free amine to the completely protected TADF, as shown below:

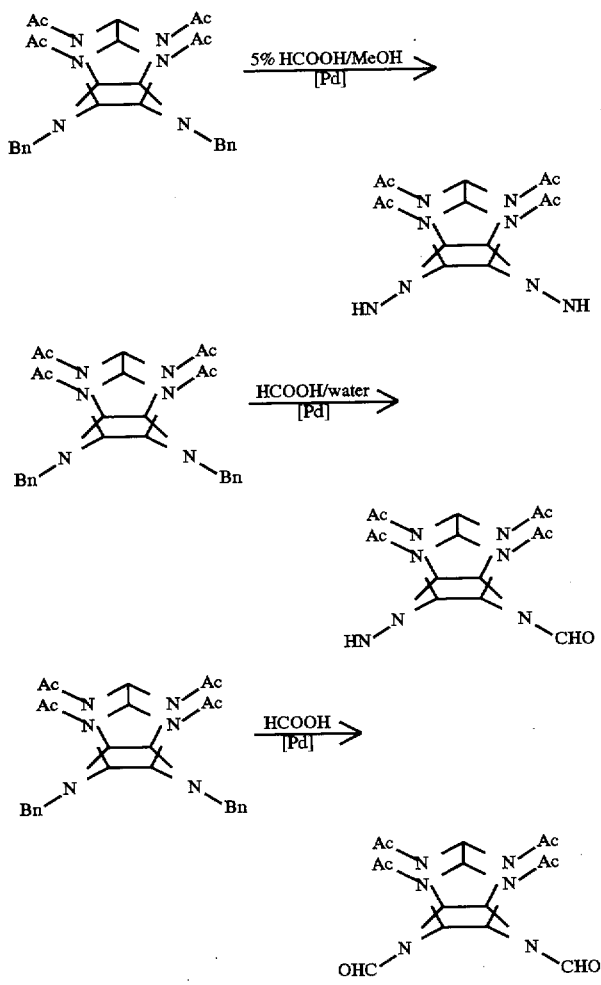

The catalyst remaining with the TADB from the previous reaction is all that is needed for this reaction. Upon addition of hydrogen, the reaction proceeds. The second hydrogenolysis reaction is slower than the first hydrogenolysis, due to the reduced activity of the last two benzyl groups towards hydrogenolysis.

The catalyst is removed by filtration, and the product is recovered by evaporation of the volatile solvents. The catalyst may be recycled and used again in the process or it may be reprocessed by the catalyst manufacturer. The product thus obtained is of a purity suitable for direct use in the nitration reaction to produce CL-20.

The following examples are offered to further illustrate the present invention. These examples are intended to be purely exemplary and should not be viewed as a limitation on any claimed embodiment.

EXAMPLE 1

Preparation of 4,10-Dibenzyl-2,6,8,12-tetraacetyl-2, 4,6,8,10,12-hexaazatetracyclo[5.5.0.0$^{5,9}$.0$^{3,11}$] dodecane ("TADB")

To a mixture of 122 kg of DMF and 70 kg (686 moles) of acetic anhydride in a 75 gallon stirred autoclave (steel reactor) were added 43.2 kg (61 moles) of HBIW, 0.78 l (7.4 moles) of bromobenzene, and 4.63 kg of a 55.3% moisture 10% palladium on carbon catalyst (dry weight of catalyst was 2.07 kg). The vessel was purged four times with hydrogen. During the purges, the temperature of the reactor rose from 21.3° C. to 25.2° C. The reaction was then stirred under 50 psi pressure of hydrogen introduced into the reaction mixture via a sparge ring. Over the next 30 minutes, the reaction temperature rose to 51.4° C. and cold water was then circulated through the jacket of the flask to control the exotherm. Approximately 140 moles of hydrogen (based on pressure drop in the hydrogen tank) were consumed during this period not counting any hydrogen consumed during the purges. Over the next 1.5 hours, another 120 moles of hydrogen were consumed with the reaction temperature then at 43.1° C. (cold water was stopped circulating when the reaction temperature dropped below 35° C.). The reaction was allowed to stir an additional 21 hours during which time another 40 moles of hydrogen were consumed (total of 300 moles versus a theoretical 250 moles for the reaction). The reactor was purged three times with nitrogen then the reaction mixture was filtered. The solids were washed with roughly 130 l of denatured ethanol to afford the desired product along with palladium catalyst slightly moist with ethanol and trace amounts of DMF as a gray solid which was used directly in the next reaction. In a total of three reactions ran as described above, a total of 85.7 kg (82–85% yield) of the product mixture were obtained.

EXAMPLE 2

Preparation of 4,10-Diformyl-2,6,8,12-tetraacetyl-2, 4,6,8,10,12-hexaazatetracyclo[5.5.0.0$^{5,9}$.0$^{3,11}$] dodecane ("TADF")

A stirred solution of 85 kg of the product mixture from Example 1 above (roughly 150 moles of TADB) in 220 kg of formic acid in a 75 gallon stirred autoclave (steel reactor) was purged 5 times with hydrogen. Over the next 4 hours, approximately 110 moles of hydrogen were consumed and the reaction temperature rose from 16.1° C. to 25.8° C. Over the next 16 hours, a further 220 moles of hydrogen were consumed with the reaction temperature at 30.4° C. near the end of that period. The reactor was purged three times with nitrogen then the catalyst was separated from the soluble product by filtration. The catalyst was washed with 200 l of water then concentrated in a wiped film evaporator operating at a pressure below 20 torr with the distillation occurring at 50° C. The wiped film evaporator and autoclave were cleaned with 40 l of water and 20 l of denatured ethanol which were added to the product. Remaining volatiles were removed by drying the product in a vacuum oven at 15 torr and 50° C. By this method, 57 kg of the desired product (86% yield from TADB) were obtained with an average of 0.46% water, 1.1% DMF, and 9.82% formic acid.

EXAMPLE 3

Palladium Catalyst Comparison

A large number of catalysts were examined under standard reaction conditions. All reactions were run using 50 g of HBIW, 125 ml of DMF, 75 ml of acetic anhydride, and 1 ml of bromobenzene. All hydrogenations were ran until hydrogen uptake ceased and for a minimum of 24 hours. Typical effective reaction times were 2–4 hours. Effectiveness in a recycle was determined by obtaining a similar yield in the first recycle to that obtained in the initial reaction. Yields with NMP were generally 3–5% higher. Many catalysts were found to be excellent in the process. Several were found to be effective in recycle. The results are reproduced below in Table 1:

TABLE 1

| Catalyst Type | Metal (%) | Loading (% to HBIW) | Yield (%) | Recycle |
|---|---|---|---|---|
| E101 NE/W | 10 | 5 | 90 | yes |
| E101 NE/W | 5 | 5 | 88 | n/a |
| E101 NO/W | 5 | 5 | 89 | no |
| E101 O/W | 5 | 10 | 84 | no |
| E101 R/D | 5 | 10 | 91 | yes |
| E107 NE/W | 10 | 10 | 88 | no |
| E107 NE/W | 5 | 10 | 86 | no |
| E117 XN/W | 10 | 5 | 80 | yes |
| E196 R/W | 5 | 5 | 89 | no |

The catalysts were obtained from Degussa Corporation, South Plainfield, N.J. The "E" designation represents palladium. The "N" and "O" designations mean the metal was predominantly in the oxide form. The "R" designation means the metal was predominantly in the metallic form. The "/W" designation means the catalyst was supplied water-wet, while the "/D" designation means the catalyst was supplied dry.

It was generally found that while certain catalysts could be used multiple times in the process without reprocessing, the yield tended to drop after first cycle and more so in further cycles. Recycling of the palladium catalyst is shown below:

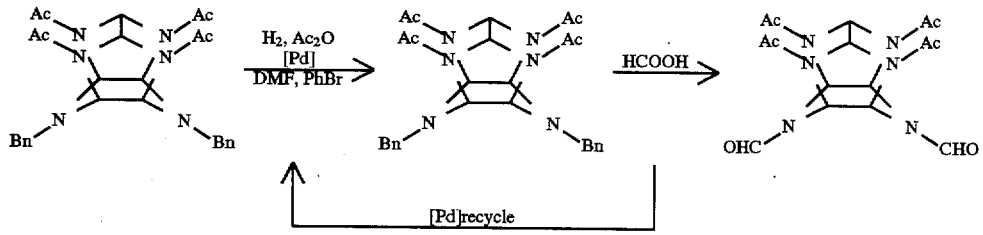

The total cost of a kilogram of catalyst was determined based on actual production runs and all costs associated with the use of the catalyst. These results, reported in Table 2, were obtained on the E101 NE/W 10% catalyst.

TABLE 2

| Quantity (kg) | Pd cost ($) | Catalyst Production ($) | Pd Recovery ($) | Pd return credit ($) | Net ($) | Catalyst Cost ($/kg) |
|---|---|---|---|---|---|---|
| 15 | 4032 | 3150 | 1100 | 2100 | 6182 | 412 |
| 25 | 6720 | 2175 | 1500 | 2770 | 7625 | 305 |
| 70 | 21475 | 6525 | 3000 | 17000 | 14000 | 200 |

These data show that only about $10 per pound of the CL-20 production costs are catalyst related at this level. Using E101 NE/W 5% catalyst results in lower palladium loss and reduced refining and processing costs. Projected to the same scale analyzed for E101 NE/W 10% catalyst, the cost per pound of CL-20 should be under $5 without any multiple use without reprocessing. Slightly lower costs will be achieved at larger scale. This is an enormous improvement over the cost reported by Nielsen at over $200 per pound of CL-20. See, copending application Ser. No. 07/292,028, filed Dec. 21, 1988 and Ser. No. 07/989,369, filed Dec. 8, 1992, and the references cited therein. This result alone shows the dramatic improvements in cost achieved using a process within the scope of the present invention.

EXAMPLE 4

Pilot Scale Preparation of 4,10-Dibenzyl-2,6,8,12-tetraacetyl-2,4,6,8,10,12-hexaazatetracyclo[5.5.0.0$^{5,9}$.0$^{3,11}$]dodecane ("TADB")

The procedure of Example 1 was scaled up for use in a 1500-gallon glass-lined reaction vessel rated for up to 100 psi. All reasonable effort was made to run the reaction according to the procedure of Example 1. However, the amount of time required to load all the reagents into the reactor and purge the reactor with inert gas before safe hydrogen introduction was significantly increased. While the hydrogen uptake began immediately on introduction and was rapid for several hours, the total amount of hydrogen consumed was roughly fifty percent of the amount theoretically required to convert all HBIW to TADB. Further, the temperature rise was significantly slower than on the smaller scale. Hydrogen uptake slowed to a near stop roughly 18 hours into the reaction.

A small aliquot was removed from the reaction mixture, the catalyst removed by filtration, and the majority of volatiles removed under reduced pressure. The $^1$H NMR of the glassy material obtained suggested a mixture of three possible isomeric compounds with two acetyl moieties and four benzyl moieties attached to an intact hexaazaisowurtzitane cage skeleton were the major constituents, shown below:

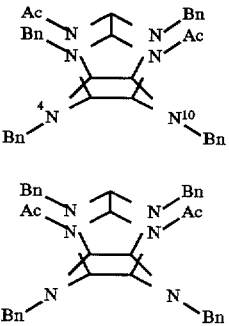

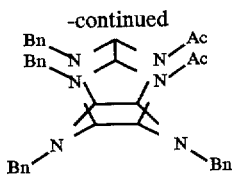

This material was stable in the reaction mixture of DMF, acetic anhydride, and acetic acid indefinitely. Later conversion to the desired TADB established that the 4 and 10 benzyl groups were not removed to any degree in this partial reaction. This was consistent with previous results that the 4 and 10 benzyl groups were not removed to any degree under the reaction conditions.

A minor component that remained initially unidentified exhibited a characteristic doublet at 64.23 in the $^1$H NMR spectrum (300 MHz). Dilution of the crude glassy material with toluene and water separated the minor component from the major constituents due to higher solubility of this compound in water. Isolation of this material allowed simple identification of the material as N-benzyl acetamide by $^1$H NMR. This identification was verified by comparison with an authentic sample of N-benzyl acetamide. The presence of this compound in the reaction mixture suggests that a portion of the HBIW starting material was hydrolyzed under the reaction conditions to afford free benzyl amine which was acetylated under the reactions conditions. This material was found to be a potent poison of the hydrogenolysis reaction. Only 0.17 g of N-benzyl acetamide was required to completely inhibit a hydrogenolysis reaction run on a scale of 25 grams of HBIW treated under standard reaction conditions!

These data suggest a scenario for the failure of this reaction to proceed to completion. With a longer time involved in introducing all reactants and purging the reactor with inert gas, there was a greater opportunity for the HBIW to be hydrolyzed by the acidic medium resulting in formation of N-benzyl acetamide that then stopped the reaction from proceeding further. This effect was verified by executing a small scale reaction under the time conditions of the large reaction and observing the same result.

Since the toluene and water extraction was found to largely remove the N-benzyl acetamide from the mixture of diacetyl compounds, the unconcentrated bulk reaction mixture was diluted with toluene and washed several times with water. The toluene layer was concentrated in a wiped film evaporator to a viscous liquid from which a solid slowly crystallized. The solid obtained was essentially free of N-benzyl acetamide based on $^1$H NMR analysis. This solid was resubjected to the original hydrogenolysis conditions and yielded TADB in excellent yield based on the amount of diacetyl compound in the reaction. This product was converted to the desired nitratable TADF under conditions of Example 2. Although the initial hydrogenation reaction failed to proceed to completion, the overall effect was small with respect to yield. The TADF obtained was indistinguishable from that made in the standard process.

EXAMPLE 5

Preparation of 4,10-Dibenzyl-2,6,8,12-tetraacetyl-2,4,6,8,10,12-hexaazatetracyclo[5.5.0.0$^{5,9}$.0$^{3,11}$] dodecane ("TADB")

To a mixture of 765 kg of DMF in a 500 gallon Pfaudler reactor (glass lined and rated to handle pressurized gases) were added 270 kg of HBIW and 7.52 kg of bromobenzene. 8.7 kg of a 54% moisture 10% palladium on carbon catalyst designation Degussa E101 NE/W (dry weight of catalyst was 4.00 kg) was washed with 20 l of DMF to remove water, and the DMF was discarded. The catalyst was added to the reactor wet with DMF. To this mixture were added 438 kg of acetic anhydride. The vessel was purged four times with hydrogen alternating with vacuum. During the purges, the temperature of the reactor rose from 22.1° C. to 23.0° C. The reaction mixture was then stirred under 60 psi pressure of hydrogen which was introduced into the reactor via a sparge valve. Over the next 50 minutes, the reaction temperature rose to 52° C. and cold water was then circulated through the reactor jacket to control the exotherm. The temperature was held at or below 55° C. for the remainder of the reaction period. The reaction mixture was allowed to stir an additional 3.5 hours. The reactor was purged three times with nitrogen then the reaction mixture was filtered. The solids were washed with roughly 200 l of methanol to afford the desired product along with palladium catalyst slightly moist with ethanol and trace amounts of DMF as a gray solid which was used directly in the next reaction. From this reaction, approximately 145 kg of the desired product, not including catalyst weight, were obtained.

It will be appreciated that the present invention provides a method for the hydrogenation of HBIW which avoids the formation of the dinitroso intermediate and provides a simpler route for the formation of CL-20. The present invention further provides a process for the hydrogenolysis of HBIW which requires less catalyst than currently known processes, thereby reducing the overall manufacturing cost of CL-20. The present invention also provides a process for the hydrogenolysis of HBIW which produces high yields of the desired end product.

The present invention may be embodied in other specific forms without departing from its essential characteristics. The described embodiments are to be considered in all respects only as illustrative and not restrictive. The scope of the invention is, therefore, indicated by the appended claims rather than by the foregoing description.

The claimed invention is:

1. A process for the hydrogenolysis of 2,4,6,8,10,12-hexabenzyl-2,4,6,8,10,12-hexaazatetracyclo[5.5.0.0$^{5,9}$.0$^{3,11}$]dodecane ("HBIW") comprising the steps of:
   (a) introducing a quantity of HBIW and a cosolvent into a reaction vessel;
   (b) adding a bromine source to the reaction vessel;
   (c) adding acetic anhydride and a palladium hydrogenolysis catalyst to the reaction vessel, wherein the hydrogenolysis catalyst is substantially free of water; and
   (d) quickly introducing hydrogen into the reaction vessel wherein HBIW is converted to tetraacetyldibenzylhexaazaisowurtzitane ("TADB").

2. A process for the hydrogenolysis HBIW as defined in claim 1, wherein the cosolvent is selected from the group consisting of N,N-dimethylformamide ("DMF"), N-methylpyrollidone ("NMP"), and 1,2-dimethoxyethane.

3. A process for the hydrogenolysis HBIW as defined in claim 1, wherein the acetic anhydride is added to the reaction vessel before the palladium hydrogenolysis catalyst.

4. A process for the hydrogenolysis HBIW as defined in claim 1, wherein the palladium hydrogenolysis catalyst is added to the reaction vessel before the acetic anhydride.

5. A process for the hydrogenolysis HBIW as defined in claim 1, wherein the bromine source is a molecule containing reactive bromine.

6. A process for the hydrogenolysis HBIW as defined in claim 1, wherein the bromine source is at least one selected from the group consisting of benzyl bromide, acetyl bromide, and bromine gas ($Br_2$).

7. A process for the hydrogenolysis HBIW as defined in claim 1, further comprising the step of purging the reaction vessel of an atmosphere capable of reacting with hydrogen by replacing said reactive atmosphere with an inert atmosphere.

8. A process for the hydrogenolysis HBIW as defined in claim 7, wherein the inert atmosphere is nitrogen.

9. A process for the hydrogenolysis HBIW as defined in claim 7, further comprising the step of mixing the HBIW, cosolvent, and bromine source within the reaction vessel under a nitrogen atmosphere prior to the addition of the acetic anhydride and the palladium hydrogenolysis catalyst.

10. A process for the hydrogenolysis HBIW as defined in claim 1, wherein hydrogen is introduced into the reaction vessel by purging the reaction vessel with hydrogen a plurality of cycles, followed by introduction of hydrogen gas under pressure.

11. A process for the hydrogenolysis HBIW as defined in claim 1, wherein the palladium hydrogenolysis catalyst is made substantially fee of water by washing the catalyst with the cosolvent.

12. A process for the hydrogenolysis HBIW as defined in claim 1, wherein the palladium hydrogenolysis catalyst comprises $Pd(OH)_2$ on carbon.

13. A process for the hydrogenolysis HBIW as defined in claim 1, wherein the hydrogenolysis catalyst is a mixture of $Pd(OH)_2$ and Pd on carbon.

14. A process for the hydrogenolysis HBIW as defined in claim 1, wherein the hydrogenolysis catalyst added to the reaction vessel in an amount less than 10% wt/wt based on the HBIW substrate.

15. A process for the hydrogenolysis HBIW as defined in claim 1, wherein the hydrogenolysis catalyst added to the reaction vessel in an amount less than 5% wt/wt based on the HBIW substrate.

16. A process for the hydrogenolysis HBIW as defined in claim 1, wherein the palladium hydrogenolysis Catalyst includes a carbon substrate and wherein the palladium metal content relative to the carbon is less than 10% by weight.

17. A process for the hydrogenolysis HBIW as defined in claim 1, wherein the palladium hydrogenolysis catalyst includes a carbon substrate and wherein the palladium metal content relative to the carbon is less than 5% by weight.

18. A process for the hydrogenolysis HBIW as defined in claim 1, wherein the TADB product precipitates onto the catalyst.

19. A process for the hydrogenolysis HBIW as defined in claim 18, further comprising the steps of filtering and washing the TADB product and catalyst with a solvent.

20. A process for the hydrogenolysis HBIW as defined in claim 19, wherein the solvent is selected from the group consisting of denatured ethanol, methanol, and isopropanol.

21. A process for the hydrogenolysis HBIW as defined in claim 19, further comprising the step of reacting the TADB product and catalyst, in a formic acid solvent, with hydrogen to form tetraacetyldiformylhexaazaisowurtzitane ("TADF").

22. A process for the hydrogenolysis of 2,4,6,8,10,12-hexabenzyl-2,4,6,8,10,12-hexaazatetracyclo[$5.5.0.0^{5,9}.0^{3,11}$]dodecane ("HBIW") comprising the steps of:

(a) introducing a quantity of HBIW and a cosolvent selected from the group consisting of N,N-dimethylformamide ("DMF"), N-methylpyrrollidone ("NMP"), and 1,2-dimethoxyethane into a reaction vessel;

(b) adding a bromine source selected from the group consisting of benzyl bromide, acetyl bromide, and bromine to the reaction vessel;

(c) adding acetic anhydride and a palladium hydrogenolysis catalyst which is substantially free of water by being washed with the cosolvent; and (d) immediately introducing hydrogen into the reaction vessel wherein HBIW is converted to tetraacetyldibenzylhexaazaisowurtzitane ("TADB") and is caused to precipitate onto the palladium hydrogenolysis catalyst.

23. A process for the hydrogenolysis HBIW as defined in claim 22, wherein hydrogen is introduced into the reaction vessel by purging the reaction vessel with hydrogen a plurality of cycles, followed by introduction of hydrogen gas under pressure.

24. A process for the hydrogenolysis HBIW as defined in claim 22, further comprising the steps of filtering and washing the TADB product and catalyst with a solvent.

25. A process for the hydrogenolysis HBIW as defined in claim 24, wherein the solvent is selected from the group consisting of denatured ethanol, methanol, and isopropanol.

26. A process for the hydrogenolysis of tetraacetyldibenzylhexaazaisowurtzitane ("TADB") comprising the steps of:

(a) introducing a quantity of TADB precipitated on a palladium hydrogenolysis catalyst and a formic acid solvent into a reaction vessel;

(b) purging the reaction vessel of an atmosphere capable of reacting with hydrogen; and (c) introducing hydrogen into the reaction vessel wherein TADB is converted to tetraacetyldiformylhexaazaisowurtzitane ("TADF").

27. A process for the hydrogenolysis of tetraacetyldibenzylhexaazaisowurtzitane ("TADB") as defined in claim 26, further comprising the steps of filtering the palladium hydrogenolysis catalyst and recovering the TADF product.

* * * * *